United States Patent [19]

Theriot et al.

[11] Patent Number: 5,633,420
[45] Date of Patent: May 27, 1997

[54] OLEFIN OLIGOMERIZATION PROCESS

[75] Inventors: Kevin J. Theriot, Baton Route; Robert G. Irwin, Prairieville, both of La.

[73] Assignee: Amoco Corporation, Chicago, Ill.

[21] Appl. No.: 532,953

[22] Filed: Sep. 22, 1995

[51] Int. Cl.[6] .................................................. C07C 2/08
[52] U.S. Cl. .................. 585/525; 585/500; 585/510; 585/514; 585/520; 585/526; 585/527; 585/529; 585/530
[58] Field of Search .............................. 585/510, 514, 585/520, 525, 527, 529, 500, 526, 530

[56] References Cited

U.S. PATENT DOCUMENTS

| | | | |
|---|---|---|---|
| 2,500,161 | 3/1950 | Seger et al. | 260/683.15 |
| 2,500,163 | 3/1950 | Garwood | 260/683.15 |
| 2,766,312 | 10/1956 | Smiuk | 260/683.15 |
| 2,806,072 | 9/1957 | Cohen et al. | 260/683.15 |
| 3,382,291 | 5/1968 | Brennan | 260/683.16 |
| 3,769,363 | 10/1973 | Brennan | 26/683.15 B |
| 3,997,621 | 12/1976 | Brennan | 260/683.15 B |
| 4,172,855 | 10/1979 | Shubkin et al. | 585/16 |
| 4,218,330 | 8/1980 | Shubkin | 252/46.6 |
| 4,409,415 | 10/1983 | Morganson et al. | 585/525 |
| 4,436,947 | 3/1984 | Morganson et al. | 585/525 |
| 4,469,912 | 9/1984 | Blewett et al. | 585/525 |
| 4,902,846 | 2/1990 | DiLeo et al. | 585/525 |
| 4,935,570 | 6/1990 | Nelson et al. | 585/329 |
| 4,950,822 | 8/1990 | DiLeo et al. | 585/310 |
| 4,956,512 | 9/1990 | Nissfolk et al. | 585/521 |
| 4,973,789 | 11/1990 | Karn et al. | 585/525 |
| 4,982,026 | 1/1991 | Karn et al. | 585/18 |
| 5,068,487 | 11/1991 | Theriot | 585/510 |
| 5,191,140 | 3/1993 | Akatsu et al. | 585/525 |
| 5,225,588 | 7/1993 | Senartne et al. | 560/71 |
| 5,241,085 | 8/1993 | Senaratne et al. | 549/396 |
| 5,250,750 | 10/1993 | Shubkin et al. | 174/17 LF |
| 5,396,013 | 3/1995 | Theriot | 585/510 |
| 5,420,373 | 5/1995 | Hope et al. | 585/525 |

*Primary Examiner*—Helane Myers
*Assistant Examiner*—Elizabeth D. Wood
*Attorney, Agent, or Firm*—Joseph DiSalvo; Stephen L. Hensley

[57] ABSTRACT

Alpha-olefin oligomers are prepared by a process which comprises contacting an oligomerizable olefin monomer with a catalyst system comprising a catalytic amount of boron trifluoride, a protic promoter, and an organic modifier selected from the group consisting of phosphate, thiophosphate, phosphine oxide, and phosphine sulfide. The oligomerizable olefin monomer is a $C_6$ to $C_{20}$ linear olefin comprising at least 50 mole % alpha olefin.

33 Claims, No Drawings

OLEFIN OLIGOMERIZATION PROCESS

TECHNICAL FIELD

This invention relates generally to the preparation of alpha-olefin oligomers which are useful as synthetic lubricants and functional fluids. More particularly, this invention relates to $BF_3$-promoter catalyst systems which use a modifier to control the oligomer product distribution and provide higher percentages of lower oligomers, especially dimers.

BACKGROUND

Alpha-olefin oligomers and their use as synthetic lubricants are well-known. The oligomers are usually hydrogenated in order to improve their stability. Early reports of such oligomeric synthetic lubricants appear in Seger et al. U.S. Pat. No. 2,500,161 and Garwood U.S. Pat. No. 2,500,163.

Oligomerization of alpha-olefins in a Group IV metal oxide bed using a $BF_3$-protic promoter catalyst is described in U.S. Pat. No. 2,766,312. Promoters referred to therein include water, carboxylic acid, alkyl halides, alcohols and ethers.

U.S. Pat. No. 2,806,072 discloses the dimerization of $C_6$–$C_{12}$ polypropylenes using a preformed $BF_3$-dialkyl ether catalyst.

Oligomerization of olefins using $BF_3$-promoter catalyst complexes of acid anhydrides, esters, ketones and aldehydes is described in U.S. Pat. No. 3,382,291.

U.S. Pat. No. 3,769,363 to Brennan discloses oligomerization of $C_6$–$C_{12}$ normal alpha-olefins, such as 1-decene, with $BF_3$ and $C_5$ carboxylic acid to improve trimer yields.

U.S. Pat. No. 3,997,621 also to Brennan describes oligomerization of $C_6$–$C_{12}$ normal alpha-olefins with $BF_3$ using alcohols or water promoters in conjunction with small amounts of methyl and ethyl esters of a $C_2$–$C_5$ monocarboxylic acid to improve trimer yields.

In U.S. Pat. No. 4,172,855 $BF_3$-promoter catalysts for grafting a second alpha-olefin onto a $C_6$–$C_{12}$ alpha-olefin dimer to form a low volatility lubricating oil is described. The promoters include glycol ethers such as ethylene glycol monomethyl ether and propylene glycol monoethyl ether, and diisobutyl ether.

U.S. Pat. No. 4,218,330 to Shubkin describes dimerization of $C_{12}$–$C_{18}$ alpha-olefin monomer with a $BF_3$-water complex and an excess of $BF_3$. Unreacted monomer is distilled from the reaction product leaving mainly dimer with minor amounts of trimer and higher oligomers. The product is hydrogenated for use as a lubricant.

U.S. Pat. No. 4,436,947 to Morganson et al. discloses oligomerization of $C_6$–$C_{20}$ olefins, such as 1-decene, with $BF_3$ and a mixture of an aliphatic alcohol, an aliphatic ketone, and a polyol. The product is mainly trimer.

U.S. Pat. No. 4,982,026 to Karn describes polymerization of $C_2$–$C_6$ alkene monomers with $BF_3$ and a strong acid, such as phosphoric acid to produce a polymer having a molecular weight of from 250 to 500 and having a high vinylidene content.

U.S. Pat. No. 5,068,487 describes a process for producing products containing predominately dimers and trimers of alpha-olefins using a $BF_3$ catalyst promoted by an alcohol alkoxylate.

U.S. Pat. No. 5,191,140 discloses a process for making alpha-olefin oligomers by use of $BF_3$ promoted by at least two of water, alcohols and anhydrides to peak the reaction at lower molecular weight product.

In U.S. Pat. No. 5,396,013 it is shown that polyethers will moderate promoted $BF_3$-catalyzed oligomerizations to provide either predominately dimer- or trimer-containing oligomers.

U.S. Pat. No. 5,420,373 discloses a process for producing predominately dimer and trimer from $C_6$–$C_{20}$ olefins, such as 1-decene, with $BF_3$ and a hydroxy carbonyl promoter—i.e., a hydroxy ketone or a hydroxy aldehyde. Secondary promoters may also be used, namely aldehydes, alcohols, alcohol alkoxylates, carboxylic acids, ethers, ketones, and their mixtures.

The particular application for which the oligomer oils are used depends largely upon their viscosity, with viscosities of about 2–10 cSt at 100° C. being preferred for general lubricating oil applications. These materials are, in general, mixtures of different percentages of dimer, trimer, tetramer, pentamer and, in the case of the higher viscosity products in this range, higher oligomers as well. To increase viscosity, processes are used which either produce more of the higher oligomers or some of the lower oligomers are removed such as by distillation.

Most lower viscosity dimer products are obtained as by-products of the production of higher viscosity synthetic oils. Because of increasing use of dimers in applications such as low temperature lubricants and drilling fluids, methods for their preferential production are of particular interest. Although higher oligomerization temperatures tend to increase dimer formation, use of such higher temperatures can cause corrosion of process equipment.

SUMMARY OF THE INVENTION

New, highly effective modifiers for $BF_3$-catalyzed oligomerization reactions have been discovered. By the practice of preferred embodiments of this invention it has been found possible to modify the promoted catalytic reaction so that product containing as much as 50% or more of dimer can be produced at high conversions, at modest reaction temperatures, and in acceptably short reaction periods.

The modifiers employed pursuant to this invention are organic phosphates, thiophosphates, phosphine oxides and phosphine sulfides.

Accordingly, in one of its embodiments this invention provides a process of preparing alpha-olefin oligomer which comprises contacting an alpha-olefin monomer which contains from about 6 to about 20 carbon atoms with a catalyst system comprising boron trifluoride, a protic promoter, and an organic phosphate, thiophosphate, phosphine oxide or phosphine sulfide.

In a preferred embodiment the foregoing process is conducted under oligomerization conditions forming a reaction mixture that contains 50 wt % or more of dimer, terminating the oligomerization in said reaction mixture, and recovering the dimer from said reaction mixture, for example, by distillation. It has been found possible to conduct the process whereby at an alpha-olefin conversion above 90%, oligomerization reaction product mixtures containing less than 5 wt % of tetramer and higher oligomer are formed, and this constitutes a particularly preferred embodiment of this invention. The preferred oligomerization conditions which form 50 wt % or more dimer are temperatures of about 30° to about 150° C. under an atmosphere comprising boron trifluoride at a pressure of about 5 to about 100 psig, and in proportions in the range of about 0.5 to about 2.00 moles of modifier per mole of promoter. The especially preferred oligomerization conditions which yield above 90% conversion and less than 5 wt % tetramer and above are olefin monomer of 1-decene, temperatures of about 40° to about 60° C. under an atmosphere comprising boron trifluoride at a pressure of about 5 to about 100 psig, in proportions of about 1.0 mole % protic promoter based on olefin monomer, and in equimolar proportions in terms of modifier per mole of promoter.

Another preferred embodiment utilizes water and/or at least one alkanol as the catalyst promoter in the each of the foregoing processes.

Still another preferred embodiment involves conducting a process of this invention using as the protic promoter an alcohol alkoxylate such as described in U.S. Pat. No. 5,068,487.

A further embodiment of this invention involves use of a modifier of this invention in the form of an oligomer or polymer of sufficient molecular weight to enable the modifier to be readily removed from the reaction product mixture on completion of the oligomerization reaction.

Still another embodiment involves using a modifier of this invention having olefinic unsaturation so that the modifier, or at least a portion thereof, can become chemically bound in the olefin oligomer product.

The above and other embodiments and features of this invention will become still further apparent from the ensuing description and appended claims.

FURTHER DESCRIPTION

The olefins used in making the oligomers are predominately (at least 50 mole %) $C_6$–$C_{20}$ straight chain (i.e., linear) monoolefinically unsaturated hydrocarbons in which the olefinic unsaturation exists in the 1- or alpha-position of the straight chain. Such alpha-olefins are available as articles of commerce, and can be made by thermal cracking of paraffinic hydrocarbons or by well-known Ziegler ethylene chain growth technology. Individual olefins can be used as well as mixtures of such olefins. Examples of olefins that can be used are 1-hexene, 1-heptene, 1-octene, 1-nonene, 1-decene, 1-undecene, 1-dodecene, 1-tridecene, 1-tetradecene, 1-hexadecene, 1-octadecene, 1-eicosene, and mixtures of two or more of such 1-olefins. Remotely branched 1-olefins such as 5-methyl-1-heptene, 6-methyl-1-heptene, 6-methyl-1-octene, 7-methyl-1-octene, 6,7-dimethyl-1-octene, 7,7-dimethyl-1-octene, 8-methyl-1-nonene, and like 1-olefins can also be used especially when used together with linear 1-olefins. The more preferred olefins are linear alpha-olefin monomers containing about 8–14 carbon atoms. The most preferred 1-olefin monomer is 1-decene.

Minor amounts of up to about 50, and usually less than 25 mole % of internal and/or vinylidene olefins can be present in the olefin monomers.

Oligomerization is effected by contacting the monomer(s) with a catalytic amount of boron trifluoride, which typically is at least about 0.002 moles per mole of olefin, together with a protic promoter and a modifier. Preferably the reaction is performed in a reaction mixture saturated with boron trifluoride or in a sealed agitated reactor under an atmosphere enriched in boron trifluoride.

Among the protic promoters that can be used are water, carboxylic acids, mineral acids, alcohols, phenols, carboxylic acid esters and anhydrides, ketones, aldehydes, hydroxy ketones, hydroxy aldehydes, alcohol alkoxylates, and mixtures of any two or more of the foregoing. Preferred are water, $C_1$ to $C_{24}$ alcohols and, more preferably, $C_1$ to $C_{12}$ alcohols, and alcohol alkoxylates such as described in U.S. Pat. No. 5,068,487. Examples of preferred alcohols include methanol, ethanol, 1-propanol, 2-propanol, 1-butanol, 2-methyl-1-propanol, 1-pentanol, 2-pentanol, 1-hexanol, 2-hexanol, 1-heptanol, 1-octanol, 2-ethyl-1-hexanol, 1-nonanol, 1-decanol, 1-undecanol, 1-dodecanol, and mixtures of two or more $C_1$ to C12 alcohols. Of these, 1-propanol and 1-butanol are particularly preferred. Examples of alcohol alkoxylates include 2-methoxyethanol, 2-ethoxyethanol, 1-methoxy-2-propanol, 4-ethoxy-1-butanol, 2-butoxyethanol, and their analogs and homologs. The protic promoter is used in an oligomerization-promoting amount, i.e., an amount that causes the $BF_3$ to function as an oligomerization catalyst, such as for example from about 0.001 to about 0.04 moles per mole of alpha-olefin monomer (s). In general the $BF_3$ is used in a molar excess relative to the quantity of promoter(s) used, typically by maintaining a pressurized atmosphere of $BF_3$ or $BF_3$ and nitrogen in the reaction vessel. The promoter can be mixed with the olefin feed or the promoter can be charged separately to the reactor, either entirely at the outset or portionwise as the oligomerization proceeds.

The organic phosphates, thiophosphates, phosphine oxides and phosphine sulfides used in the practice of this invention can either contain no additional functionality in the molecule or they can contain additional functionality in the organic portion of the molecule, provided the functionality is such that it does not significantly impair the effectiveness of the modifier. Linkages or substituents in one or more of the organic moieties in the modifier that do not impair the effectiveness of the modifiers and that thus can be present therein are the following: halide, hydrocarbyloxy, hydrocarbylthio, ether oxygen linkage, thioether sulfur linkage, nitro, hydrocarbylsilyl, carbonyl, and thiocarbonyl.

A few examples of modifiers having additional non-harmful functionality are:
tris(2-chloroethyl)phosphate
tris(2-chloropropyl)phosphorothioate
bis(phenyl)-p-nitrophenylphosphate
tris(2-butoxyethyl)phosphate
2,4-dichlorophenyl bis(phenyl)phosphate
tris(4-trifluoromethylphenyl)phosphine oxide
tris(4-methoxyphenyl)phosphine sulfide
tris(2,3-dibromopropyl)phosphate
tris(2-carbamoylethyl)phosphine oxide
tris(p-nitrophenyl)phosphate
tris(2-methoxyethoxyethyl)phosphorothioate
poly(dipropyleneglycol) phenyl phosphate
poly(dipropyleneglycol) phenyl phosphorothioate
tris(2-methoxyphenyl)phosphine oxide
tris(4-nitrophenyl)phosphorothioate.

In general, the preferred modifiers are those that contain no additional functionality in the molecule. In other words, the preferred modifiers are tris(hydrocarbyl)phosphates, tris (hydrocarbyl)thiophosphates, tris(hydrocarbyl)phosphine oxides, and tris(hydrocarbyl)phosphine sulfides.

The organic phosphate and thiophosphate modifiers can be tertiary esters having one phosphate or thiophosphate moiety in the molecule or tertiary esters having more than one phosphate or thiophosphate moiety in the molecule such as tertiary diphosphates and the various sulfur analogs thereof. In this connection, unless the context clearly indicates otherwise, the term "thiophosphate" is used in this specification and in the claims in a generic sense to encompass compounds in which the pentavalent phosphorus atom has one, two, three or four sulfur atoms directly bonded thereto, and when the number of sulfur atoms is less than four, one sulfur atom can be bonded to the phosphorus atom by a double bond, or alternatively, an oxygen atom can be bonded to the phosphorus atom by a double bond. Preferred trihydrocarbylphosphate and trihydrocarbylthiophosphate modifiers can be depicted by the formula:

$$(R^1X-)(R^2X-)(R^3X-)P=X$$

where each X is, independently, an oxygen atom or a sulfur atom, and where $R^1$, $R^2$, and $R^3$ are, independently, separate hydrocarbyl groups, or where $R^1$ and $R^2$ taken together constitute a single hydrocarbyl group forming a heterocyclic ring system in which the phosphorus atom and two X atoms are included the ring system, or where $R^1$, $R^2$ and $R^3$ taken together constitute a single hydrocarbyl group forming a bicyclic heterocyclic ring system in which the phosphorus atom and three X atoms are included the ring system. $R^1$, $R^2$ and $R^3$ can be, independently, saturated or olefinically unsaturated aliphatic, cycloaliphatic or aromatic groups. Normally, $R^1$, $R^2$ and $R^3$ will each contain up to about 30 carbon atoms, and more preferably up to about 12 carbon atoms each.

Examples of compounds having a single phosphorus atom in the molecule in which $R^1$, $R^2$ and $R^3$ are separate hydrocarbyl groups include trialkylphosphates, trialkenylphosphates, tricycloalkylphosphates, tricycloalkenylphosphates, triarylphosphates, triaralkylphosphates, (alkenyl)(dialkyl)phosphates, (cycloalkyl)(dialkyl)phosphates, (cycloalkenyl)(dialkyl) phosphates, (aryl)(dialkyl)phosphates, (aralkyl)(dialkyl) phosphates, (alkyl)(dialkenyl)phosphates, (cycloalkyl) (dialkenyl)phosphates, (cycloalkenyl)(dialkenyl) phosphates, (aryl)(dialkenyl)phosphates, (aralkyl) (dialkenyl)phosphates, (alkyl)(dicycloalkyl)phosphates, (alkenyl)(dicycloalkyl)phosphates, (cycloalkenyl) (dicycloalkyl)phosphates, (aryl)(dicycloalkyl)phosphates, (aralkyl)(dicycloalkyl)phosphates, (alkyl)(dicycloalkenyl) phosphates, (alkenyl)(dicycloalkenyl)phosphates, (cycloalkyl)(dicycloalkenyl)phosphates, (aryl) (dicycloalkenyl)phosphates, (aralkyl)(dicycloalkenyl) phosphates, (alkyl)(diaryl)phosphates, (alkenyl)(diaryl) phosphates, (cycloalkyl)(diaryl)phosphates, (cycloalkenyl) (diaryl)phosphates, (aralkyl)(diaryl)phosphates, (alkyl) (diaralkyl)phosphates, (alkenyl)(diaralkyl)phosphates, (cycloalkyl)(diaralkyl)phosphates, (cycloalkenyl)(diaralkyl) phosphates, (aryl)(diaralkyl)phosphates, and their sulfur analogs having one, two, three or all four of the oxygen atoms of the foregoing tertiary phosphate esters replaced by a corresponding number of sulfur atoms. Tertiary phosphates and thiophosphates having three different types of hydrocarbyl groups in the molecule (e.g., any three different members selected from alkyl, alkenyl, cycloalkyl, cycloalkenyl, aryl and aralkyl groups) are also suitable. Combinations of two or more of any of the foregoing phosphates, combinations of two or more of any of the foregoing thiophosphates, and combinations of one or more of any of the foregoing phosphates together with one or more of any of the foregoing thiophosphates can be used, if desired.

Phosphate and thiophosphate modifiers having a single phosphorus atom in the molecule and in which $R^1$ and $R^2$ form a heterocyclic ring system with the phosphorus atom are glycol phosphates and glycol thiophosphates so-named because they are often prepared by from a glycol or sulfur analog thereof, e.g., a 1,2-diol, 1,3-diol, 1,2-dithiol or 1,3-dithiol. The hydrocarbyldioxo group or hydrocarbyldithio group typically contains from 2 to about 20 carbon atoms and has the formula:

$$-X-\underset{R^5}{\overset{R^4}{C}}-(C)_n-\underset{R^7}{\overset{R^6}{C}}-\underset{R^9}{\overset{R^8}{C}}-X-$$

where X is as defined above, n is zero or 1, and each of $R^4$, $R^5$, $R^6$, $R^7$, $R^8$, and $R^9$ is, independently, a hydrogen atom or a hydrocarbyl group.

Phosphate and thiophosphate modifiers having a single phosphorus atom in the molecule and in which $R^1$, $R^2$ and $R^3$ form a bicyclic ring system with the phosphorus atom and the three oxygen and/or sulfur atoms are exemplified by such compounds as 4-ethyl-2,6,7-trioxa-1-phosphabicyclo [2.2.2]octane-1-oxide, 4-ethyl-2,6,7-trioxa-1-phosphabicyclo[2.2.2]octane-1-sulfide, 4-butyl-2,6,7-trioxa-1-phosphabicyclo[2.2.2]octane-1-oxide, and like compounds. Compounds of this type are prepared by reacting suitable branched polyols or polythiols whereby three hydroxyl or thiol groups become bonded to the same phosphorus atom and in so doing create a bicyclic structure. Examples of suitable triols of this type include 1,1,1-trimethylolethane, 1,1,1-trimethylolpropane, 1,1,1-trimethylolbutane, 1,1,1-trimethylolpentane, and 1,1,1-trimethylolhexane. Sulfur analogs of such compounds may also be used.

Preferred phosphates and thiophosphates are those that are easily prepared from readily available low-cost starting materials or that are themselves readily available as articles of commerce at relatively low cost. A few examples of specific compounds are trimethylphosphate, triethylphosphate, triallylphosphate, tributylphosphate, tri (2-ethylhexyl)phosphate, triphenylphosphate, tricresyl phosphate, (cresyl)-di(phenyl)phosphate, tripropylphosphorothioate, triphenylphosphorothioate, di(isobutyl)(styryl)phosphorodithioate, di(propyl) (norbornyl)phosphorodithioate, triamylphosphorotetrathioate, trilaurylphosphorotetrathioate, phenyl neopentylene glycol phosphate, phenyl neopentylene glycol phosphorothioate, and their homologs and analogs.

Phosphates and thiophosphates having more than one phosphate or thiophosphate functional group per molecule are exemplified by the di-, tri-, tetra-, and higher polyphosphates and polythiophosphates. These can be represented by the general formula:

$$(R^{10}X-)[(R^{10}X-)P(=X)-XR^{11}-]_mP(=X)(-XR^{10})(-R^{10})$$

where X is as defined above, m is an integer from 1 to about 10 or more, and each $R^{10}$ is, independently, a univalent hydrocarbyl group each of which typically contains up to about 30 carbon atoms, and more preferably up to about 12 carbon atoms, and each $R^{11}$ is, independently, a divalent hydrocarbyl group such as alkylene, cycloalkylene, arylene, etc., which typically has up to about 18 carbon atoms. A few illustrative examples of such compounds are bis(4-ethylphenyl)pentaerythritol diphosphate, bis(2,4-dimethylphenyl) pentaerythritol diphosphorothioate, dibutyl pentaerythritol diphosphate, dicyclohexyl pentaerythritol diphosphorodithioate, distearyl pentaerythritol diphosphorothioate, tetraethyl butylene glycol diphosphate, tetraphenyl poly(propyleneglycolphosphate) (each $R^{10}$ is phenyl, each X is an oxygen atom, $R^{11}$ is trimethylene and m is 7), tris(ethylene glycol) diphosphate, and analogous compounds.

Preferred trihydrocarbylphosphine oxide and trihydrocarbylphosphine sulfide modifiers used pursuant to this invention can be depicted by the formula:

$$(R^{12}-)(R^{13}-)(R^{14}-)P=X$$

where $R^{12}$, $R^{13}$ and $R^{14}$ are, independently, hydrocarbyl groups bonded to the phosphorus atom and thus are, independently, aliphatic, cycloaliphatic or aromatic, and when aliphatic or cycloaliphatic, any or all of $R^{12}$, $R^{13}$ and $R^{14}$ can be saturated or olefinically unsaturated. Normally, $R^{12}$, $R^{13}$ and $R^{14}$ will each contain up to about 30 carbon atoms, and more preferably each will contain up to about 12 carbon atoms. It is also possible for two of $R^{12}$, $R^{13}$ and $R^{14}$ to form a heterocyclic ring system including the phosphine oxide or phosphine sulfide moiety. When two of $R^{12}$, $R^{13}$ and $R^{14}$ are in the form of a single hydrocarbyl group, the third group can be any univalent hydrocarbyl group such as referred to hereinabove, and the cyclic tertiary phosphine oxide or cyclic tertiary phosphine sulfide will typically contain up to about 24 and preferably up to about 18 carbon atoms in the molecule.

As indicated above, olefin functionality may be included in the modifier. In such cases the modifier may become incorporated into the oligomer, and this may be desirable when using the oligomer for certain heavy duty lubrication applications, as the phosphorus (and sulfur if present) can contribute antiwear and/or extreme pressure properties to the lubricant.

One preferred class of modifiers of this invention are the polymeric phosphates and polymeric thiophosphates formed by polymerizing a terminally olefinically unsaturated tertiary phosphate or thiophosphate ester with a suitable olefin polymerization catalyst system such as an alkyl aluminum compound and a titanium or zirconium halide such as titanium tetrachloride or zirconium tetrachloride. Examples of such unsaturated tertiary phosphate and unsaturated tertiary thiophosphate esters include (allyl)(dimethyl)phosphate, (3-butenyl)di(ethyl)phosphate, di(allyl)(phenyl)phosphate, and their monothio, dithio, trithio and tetrathio analogs. An advantageous feature of such polymeric modifiers is their ready separability from the oligomerization reaction product mixture.

While normally a single modifier is used in the process of this invention, suitable mixtures of two or more modifiers can be employed, if desired.

In conducting the process of this invention the alpha-olefin or mixture of alpha-olefins, boron trifluoride, protic promoter and modifier can be charged to the reactor in any suitable sequence. Preferably, however, the modifier should be present before any substantial amount of oligomerization has occurred. In this way the maximum beneficial reaction modifying effect of the modifier can be realized.

The reaction can be carried out as a batch, continuous, or semi-continuous process at temperatures which typically are in the range of 0° to 200° C., and preferably in the range of about 30° to about 150° C. More preferably, the temperature is maintained in the range of about 30° to about 60° C., and especially in the range of about 40° to about 60° C. The reaction is typically conducted at pressures ranging from atmospheric up to, for example, 1000 psig, and preferably in the range of about 5 to about 100 psig. The progress of the reaction can be monitored, if desired, by taking samples of the oligomerization mixtures at suitable periods during the course of the reaction and subjecting the sample to gas chromatographic (GC) analysis. In this connection, all references in this specification and in the claims to weight percentages of oligomer components in the oligomerization reaction product mixture or olefin conversion percentages are based on GC area percentages in which the analyses are conducted using a Hewlett Packard 5890 gas chromatograph equipped with a flame ionization detector and a methyl siloxane column operated under the following conditions: initial temperature=100° C.; final temperature=350° C.; Rate=15° C./minute.

The reaction can be conducted in a single stirred reactor or in a series of reactors.

To terminate the oligomerization reaction when the desired product distribution and olefin conversion have been achieved, the dimer enriched reaction mixture can be quenched with or in water or an aqueous solution, such as a solution of a salt or a base, or more preferably a solution of a strong base such as sodium hydroxide or potassium hydroxide. The organic phase is recovered and unless the oligomeric product is to be used in the form produced, the reaction product is distilled to recover the product fraction(s) desired. Unreacted olefin can be recovered and recycled.

In most cases the modifiers are used in proportions relative to the promoter that will peak the oligomerization at the dimer stage, but in some cases the proportions can be adjusted for peaking at the trimer stage. Thus in general the ratio of modifier to promoter will usually fall somewhere within the range of from about 0.1 to about 10 moles of modifier per mole of promoter, and typically within the range of from about 0.5 to about 2 moles of modifier per mole of promoter. For producing product containing at least 50 wt % dimer, the preferred proportions fall in the range of from about 0.75 to about 1.25 moles of modifier per mole of promoter. Where the modifier is difunctional (e.g., when a diphosphate, etc., is used) the molar amount of the modifier should be reduced by about one-half, and further proportionate reductions should be considered for use when the modifier being used is in the form of an oligomer or polymer. It should be understood that one should use a suitable ratio for achieving the particular results desired under the particular reaction conditions and with the particular materials selected for use. Thus the ratio that will best serve the needs of the situation at hand can be determined by performing a few oligomerizations using procedures such as given in the following illustrative examples.

EXAMPLES

1-Decene, 1-butanol (1.0 mole % based on 1-decene) and the amount of the modifier (see in Table I), are charged to a reactor equipped with cooling means, stirring means and inlet/outlet ports. The reactor is sealed and pressurized (10 psig) with boron trifluoride, and the temperature of the stirred mixture is maintained at 50° C. by external cooling for the duration of the reaction. Periodic samples are taken for GC analysis to monitor the progress of the reaction. To terminate the reaction, the reactor is vented into a caustic scrubber, purged with nitrogen, and the reactor contents are drained into 10% aqueous caustic solution. The product is then washed twice with water. The final product mixture is analyzed by GC for product composition.

In Table I the modifiers are identified as follows: A is triethyl phosphate and B is tributyl phosphine oxide. For comparative purposes the following trivalent phosphorus compounds were used: triethyl phosphite and tributyl phosphine, identified in the Table I as C and D, respectively. The Control of Table I was a run carried out in the same manner as the above examples except that no modifier was used.

TABLE I

| Example | Modifier (mole %) | Time, min. | $C_{20}$, % | $C_{30}$, % | $C_{40}$, % | $C_{50}$, % | Conversion, % |
| --- | --- | --- | --- | --- | --- | --- | --- |
| 1 | A (1.0) | 120 | 50.5 | 39.5 | 3.3 | 0.2 | 93.4 |
| 2 | B (1.0) | 180 | 54.3 | 33.9 | 2.7 | 0.2 | 91.1 |
| Comp. 3 | C (1.0) | 180 | 6.0 | 0.5 | — | — | 6.5 |
| Comp. 4 | D (1.0) | 180 | — | — | — | — | No reaction |
| Control | None | 120 | 11.8 | 65.2 | 16.7 | 3.8 | 97.6 |

It will be noted from a comparison of the results of the Comparative Examples 3 and 4 versus the Control run that the trivalent phosphorus compounds were not only ineffective, but they actually suppressed the reaction. In fact, one of them (tributyl phosphine) completely inhibited the reaction. In sharp contrast, the pentavalent phosphorus modifiers of this invention gave very desirable peaking or enrichment of the reaction product at the dimer stage, and additionally these results were achieved at high olefin conversions.

The entire disclosure of each and every U.S. patent referred to in any portion of this specification is incorporated herein by reference for all purposes.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process of preparing alpha-olefin oligomer which comprises contacting an oligomerizable olefin monomer with a catalyst system comprising a catalytic amount of boron trifluoride, a protic promoter employed in an oligomerization promoting amount, an organic modifier selected from the group consisting of phosphate, phosphine oxide, and phosphine sulfide at a pressure from about atmospheric to about 1000 psig, a temperature of about 0° C. to about 200° C., and a molar ratio in the range of about 0.1 moles to about 10 moles of modifier per mole of promoter wherein the olefin monomer is a $C_6$ to $C_{20}$ linear olefin comprising at least 50 mole % alpha olefin.

2. A process according to claim 1 wherein the protic promoter is selected from the group consisting of water, at least one alcohol, and mixtures thereof.

3. A process according to claim 1 wherein the oligomerization is carried out at a pressure from about 5 psig to about 100 psig, a temperature of about 30° C. to about 60° C., employing about 1.0 mole % of promoter based on olefin oligomer, and a molar ratio in the range of about 0.5 moles to about 2.0 moles of modifier per mole of promoter.

4. A process according to claim 3 wherein the temperature is maintained in the range of about 40° C. to about 60° C.

5. A process according to claim 1 wherein the protic promoter is an alcohol alkoxylate.

6. A process according to claim 1 wherein the olefin monomer has from 8 to 14 carbon atoms.

7. A process according to claim 1 wherein the olefin monomer is 1-decene.

8. A process according to claim 1 wherein the modifier is a trihydrocarbyl phosphate.

9. A process according to claim 1 wherein the modifier is a trihydrocarbyl phosphine oxide.

10. A process of preparing alpha-olefin oligomer which comprises oligomerizing an oligomerizable olefin monomer with a catalyst system comprising a catalytic amount of boron trifluoride, a protic promoter employed in an oligomerization promoting amount, a modifier selected from the group consisting of tri-substituted organic phosphates, tri-substituted organic phosphine oxides and tri-substituted organic phosphine sulfides, at a temperature in the range of about 0° to about 200° C., and under an atmosphere comprising boron trifluoride at a pressure from about atmospheric to about 1000 psig wherein the olefin monomer is a $C_6$ to $C_{20}$ linear olefin comprising at least 50 mole % alpha olefin.

11. A process according to claim 10 wherein the olefin monomer is linear alpha-olefin.

12. A process according to claim 10 wherein the protic promoter is selected from the group consisting of an alcohol and a combination of alcohols, and wherein the modifier is selected from the group consisting of a trihydrocarbyl phosphate, a trihydrocarbyl phosphine oxide, and a trihydrocarbyl phosphine sulfide.

13. A process according to claim 10 wherein the olefin monomer is 1-decene.

14. A process according to claim 10 wherein the temperature is maintained in the range of about 30° to about 60° C. and wherein the pressure is maintained in the range of about 5 to about 100 psig.

15. A process according to claim 11 wherein the modifier is selected from the group consisting of a trialkyl phosphate and a trialkyl phosphine oxide.

16. A process of preparing alpha-olefin oligomer which comprises oligomerizing linear olefin monomer comprising at least 50 mole % alpha olefin having in the range of 8 to 14 carbon atoms in the molecule with a catalyst system comprising a catalytic amount of boron trifluoride, a protic promoter employed in the range of about 1.0 mole % based on olefin monomer, and a modifier selected from the group consisting of organic phosphates, organic phosphine oxides, and organic phosphine sulfides, at a temperature in the range of about 30° to about 150° C., under an atmosphere comprising boron trifluoride at a pressure in the range of 5 psig to about 100 psig, and in proportions in the range of about 0.5 to about 2 moles of modifier per mole of promoter, to thereby form an oligomerization product mixture containing at least about 50 wt % of dimer.

17. A process according to claim 16 wherein the protic promoter is selected from the group consisting of water, an alcohol, and a combination of these.

18. A process according to claim 17 wherein the olefin monomer is 1-decene.

19. A process according to claim 16 wherein the oligomerization is terminated by quenching the said oligomerization product mixture with water or an aqueous solution.

20. A process according to claim 16 wherein said proportions are in the range of about 0.75 to about 1.25 moles of modifier per mole of promoter.

21. A process according to claim 16 wherein the temperature is maintained in the range of about 30° to about 60° C.

22. A process according to claim 16 wherein the olefin monomer is 1-decene, and wherein said proportions are in the range of about 0.75 to about 1.25 moles of modifier per mole of promoter.

23. A process according to claim 16 wherein the protic promoter is an alcohol, and wherein the modifier is selected from the group consisting of a trihydrocarbyl phosphate and a trihydrocarbyl phosphine oxide.

24. A process according to claim 23 wherein the olefin monomer is 1-decene, and wherein said promoter and said modifier are employed in equimolar proportions.

25. A process according to claim 24 wherein the temperature is maintained in the range of about 40° to about 60° C.

26. A process according to claim 25 wherein the protic promoter is selected from the group consisting of 1-butanol and 1-propanol.

27. A process according to claim 16 wherein the temperature is maintained in the range of about 40° to about 60° C. and wherein said proportions are in the range of about 0.75 to about 1.25 moles of modifier per mole of promoter and wherein said oligomerization product mixture contains less than 5 wt % of tetramer.

28. A process according to claim 1 wherein the phosphate is a thiophosphate.

29. A process according to claim 10, wherein the phosphate is a thiophosphate.

30. A process according to claim 12 wherein the phosphate is a thiophosphate.

31. A process according to claim 16 wherein the phosphate is a thiophosphate.

32. A process according to claim 12 wherein the alcohol is an alcohol alkoxylate.

33. A process according to claim 17 wherein the alcohol is an alcohol alkoxylate.

* * * * *